US012678114B2

(12) United States Patent
Tashenov

(10) Patent No.: US 12,678,114 B2
(45) Date of Patent: Jul. 14, 2026

(54) METHOD FOR MULTI-ENERGY X-RAY IMAGING, X-RAY FACILITY, TREATMENT SYSTEM, COMPUTER PROGRAM AND ELECTRONICALLY READABLE DATA CARRIER

(71) Applicant: Siemens Healthcare GmbH, Erlangen (DE)

(72) Inventor: Stanislav Tashenov, Heroldsbach (DE)

(73) Assignee: Siemens Healthineers AG, Forchheim (DE)

(*) Notice: Subject to any disclaimer, the term of this patent is extended or adjusted under 35 U.S.C. 154(b) by 471 days.

(21) Appl. No.: 18/198,541

(22) Filed: May 17, 2023

(65) Prior Publication Data

US 2023/0380785 A1     Nov. 30, 2023

(30) Foreign Application Priority Data

May 25, 2022     (DE) ..................... 10 2022 205 295.1

(51) Int. Cl.
*A61B 6/00*          (2024.01)
*A61B 6/03*          (2006.01)
*A61B 6/42*          (2024.01)

(52) U.S. Cl.
CPC .............. *A61B 6/482* (2013.01); *A61B 6/032* (2013.01); *A61B 6/4241* (2013.01)

(58) Field of Classification Search
CPC ....... A61B 6/481; A61B 6/482; A61B 6/5235; A61B 6/032
See application file for complete search history.

(56) References Cited

U.S. PATENT DOCUMENTS

| | | | |
|---|---|---|---|
| 4,887,604 A | 12/1989 | Shefer et al. | |
| 2014/0005533 A1* | 1/2014 | Grasruck | ............. A61B 6/4035 |
| | | | 600/431 |
| 2018/0325479 A1* | 11/2018 | Flohr | ................... A61K 9/0019 |
| 2022/0048788 A1* | 2/2022 | Chakravarty | ...... A61K 47/6929 |

FOREIGN PATENT DOCUMENTS

DE          102015212369 A1          1/2016

OTHER PUBLICATIONS

Negussie, Ayele H., et al. "Synthesis, characterization, and imaging of radiopaque bismuth beads for image-guided transarterial embolization." Scientific reports 11.1 (2021): 1-12.

* cited by examiner

*Primary Examiner* — Dani Fox
(74) *Attorney, Agent, or Firm* — Lempia Summerfield Katz LLC

(57) ABSTRACT

A method is provided for multi-energy X-ray imaging of a field of view in order to display a contrast material, located in the field of view, having an atomic number of at least 65, (e.g., at least 73), and/or a k-edge of at least 60 keV. In the method, two image datasets having different X-ray spectra are recorded and are combined in order to ascertain display information of the contrast material, wherein the X-ray spectra are generated by using at least one spectrally acting filter, starting from a source spectrum of an X-ray source in such a way that the value of their differential spectrum has a maximum, which includes a range, beginning at the k-edge of the contrast material, of higher absorption by the contrast material.

21 Claims, 8 Drawing Sheets

METHOD FOR MULTI-ENERGY X-RAY IMAGING, X-RAY FACILITY, TREATMENT SYSTEM, COMPUTER PROGRAM AND ELECTRONICALLY READABLE DATA CARRIER

The present patent document claims the benefit of German Patent Application No. 10 2022 205 295.1, filed May 25, 2022, which is hereby incorporated by reference in its entirety.

TECHNICAL FIELD

The disclosure relates to a method for multi-energy X-ray imaging of a field of view in order to display a contrast material, located in the field of view, having an atomic number of at least 65, (in particular at least 73), and/or a k-edge of at least 60 keV, wherein two image datasets having different X-ray spectra are recorded and are combined in order to ascertain display information of the contrast material. The disclosure also relates to an X-ray facility, to a treatment system, to a computer program, and to an electronically readable data carrier.

BACKGROUND

Multi-energy X-ray imaging, (e.g., multi-energy computed tomography (CT), multi-energy fluoroscopy, or multi-energy radiography), is basically known in the prior art and based thereon, to record a plurality of X-ray image datasets with different X-ray spectra, X-ray spectra of different spectral distribution, therefore. Particularly known in this connection is dual-energy X-ray imaging in which exactly two image datasets are recorded with different X-ray spectra, customarily with different maximum energies in this case. Conventionally, a low-energy spectrum and a high-energy spectrum are used as the different X-ray spectra in the prior art, and these may be generated by different applied tube voltages at the X-ray source, it being possible, for example, for established tube voltages such as 80 kV, 100 kV, 120 kV, or 140 kV, as well as values therebetween to be used. The different X-ray spectra, which have, in particular, different maximum energies, may be generated, in particular with time-delayed recording, by a single X-ray source, with computed tomography facilities having two X-ray sources that may be used in computed tomography in order to be able to simultaneously record projection images and thus image datasets of two energy spectra that are to be reconstructed therefrom.

Multi-energy X-ray imaging is particularly suitable for differentiating materials having different absorption properties. Apart from applications in material testing, medical-technical applications have also become known in this connection in which, for example, from image datasets which were recorded with different X-ray spectra, material information in respect of materials with a mean atomic number is derived, for example with regard to iodine and/or calcium. Thus, for example, iodine images may be derived from the combination of image datasets, with appropriate material breakdown techniques, which ultimately combine image data from the image datasets in a particular manner, being basically known in the prior art.

Even if multi-energy-computed tomography imaging is frequently cited as an example below, two-dimensional multi-energy imaging approaches, in particular in medical technology, have also increased in importance. In particular, it has been proposed with regard to digital subtraction angiography (DSA) that instead of this multi-energy radiography, in particular dual-energy digital radiography is used because a precondition of DSA is that the patient moves as little as possible, and this is not always possible in moving organs. This applies, for example, to the heart or organs close to the diaphragm, (e.g., liver and kidneys), owing to the respiratory movement. Problems may result for DSA also when imaging the intestines, which are moving. Movement artifacts may be reduced with dual-energy imaging since the two image datasets may be recorded with a minimum delay therebetween, so the movement is also minimized.

Computed tomography was generally also proposed to check, following the administration of medical active agents, correct positioning or accumulation thereof in the human body, specifically in a target area of the human body. One important application in this connection is targeted embolization of blood vessels, for example, blood vessels supplying a tumor. In this case, an embolization agent is administered, which accumulates in a particular portion of at least one blood vessel and is intended to occlude it at least partially, with it also having been proposed to add chemical and/or radioactive active ingredients to the embolization agent. In the case of chemical active ingredients, reference is made to transarterial chemoembolization (TACE). In the case of radioactive active ingredients, reference is made to selective internal radiation therapy (SIRT). A primary field of application of such embolization methods is the treatment of advanced-stage liver cancer.

For example, microparticles, (e.g., microbeads), loaded with the chemotherapeutic or radiation therapeutic active ingredient, may be used as the embolization agent. Such microparticles may be injected, for example, with fluoroscopic guidance. The microparticles are customarily not visible in X-ray images, however, so it has been proposed that they are mixed with iodine-based contrast agents or lipiodol oil.

In this connection, however, the success of therapy greatly depends on the accuracy of the embolization. In particular, the lesion to be treated, in particular a tumor, should be embolized with an adequate quantity of the active ingredient, wherein, on the other hand, healthy tissue should be spared as far as possible. In some cases, multiple selective embolization takes place with extremely high local doses in order to achieve optimum therapy success. For example, in the case of SIRT, multiple selective embolization with a dose of 100 Gy per lesion in the case of liver cancer increased the survival time from six months to 14 months. Such high doses may only be selectively administered in order to spare healthy tissue. Monitoring of the embolized volume is extremely important with selective embolization. Checking the embolization volume is a difficult task which has not yet been completely satisfactorily solved.

In TACE, it has been proposed that the accumulation of the embolization agent is checked after administration by X-ray imaging, in particular cone beam computed tomography (CBCT). This has the drawback that during or after TACE, the computed tomography imaging shows the distribution of the liquid contrast agent in the tissue. However, the distribution of the liquid contrast agent changes quickly since it is washed out of the tissue again. The contrast displayed in cone beam computed tomography does not correspond to the accumulated embolization agents, in particular microparticles, therefore.

In SIRT, it has been proposed that radiopaque embolization agents, in particular microparticles, are used. Radiopacity may be achieved by loading the microparticles with a radiopaque material, for example iodine or barium. If it were no longer necessary to mix liquid contrast agent with the embolization agent, the computed tomography imaging would show the exact position of the embolization agent and not that of the contrast agent.

Clinical practice has found, however, that the radiopacity of such embolization agents accumulated, in particular, with iodine is not good enough for checking the correct accumulation of the embolization agent in the field of view. Furthermore, such embolization agents are customarily still mixed with iodine-containing contrast agents in order to monitor and control the buoyancy and the flow of the microparticles.

One possible solution to this problem would be the use of a dual-energy approach, so the iodine content may be separated from other materials in the image. However, this would still not provide adequate visibility of the microparticles of the embolization agent and, in the presence of liquid contrast agent, the microparticles may still not be meaningfully separated from the agent.

In SIRT, following a procedure the embolized volume is controlled by a combination of computed tomography (CT) and Single Photon Emission Computed Tomography (SPECT). This has two significant drawbacks. Firstly, the combination of computed tomography and SPECT may indeed disclose the position of the radioactive active ingredient, but the patient has to be taken to an appropriate nuclear medicine laboratory or to an appropriate examination room. An extremely long interruption in treatment is thus necessary. Furthermore, the SPECT/CT combination has a low spatial resolution, for example, in the order of a few millimeters, and this is much lower than the spatial resolution of other computed tomography approaches, in particular cone beam computed tomography. The situation may then occur where this resolution is not adequate for determining the exact position of the embolization agent. For example, some organs or anatomical structures, for which there is a risk of a collateral embolization, cannot be identified. Furthermore, the resolution is not adequate for checking whether the overlap of the segmented tumor volume with the embolized volume. A good overlap is the precondition for successful treatment and good results for the patient, for example, tumor suppression and extending life expectancy, however.

Here too it would be possible to consider providing the embolization agent with a radiopaque material, for example, iodine. However, with SIRT only very few microparticles are accumulated in the tissue, making visualization difficult.

Use of a contrast material having a high atomic number as the radiopaque material has already been contemplated in the case of such embolization methods, but also in other individual applications. Since a carrier material, (e.g., a plastic carrier material), is customarily used for microparticles, (e.g., beads (pearls)), which form embolization agents, the properties of this material also have to be considered in the further embodiment. A plastics material of the microparticles has a lower density than saline solution or contrast agent, so the microparticles experience buoyancy. This means that plastic-microparticles do not mix well with the carrier fluid, in particular saline solution or contrast agent. For optimum mixing, the microparticles may have a density that matches the density of the carrier fluid. This may be achieved by adding metal powder to the carrier material, in particular plastic carrier material. This metal powder also results in the microparticles becoming radiopaque.

The radiopacity of the microparticles is then defined by the X-ray absorption properties of the metal powder and the quantity of powder per microparticle. Since the quantity of the metal powder is specified by the required density of the microparticle for the buoyancy adjustment, the radiopacity may only be adjusted by the selection of the contrast material, of the metal in this case. A higher radiopacity per unit weight is advantageous. The higher radiopacity per unit weight is achieved by heavier contrast materials, in particular heavier metals, generally speaking contrast materials having a higher atomic number therefore, for the following reasons.

Firstly, the weight per atom scales with the atomic number (atomic number, Z). Secondly, the photoelectric cross-section in the case of X-ray energies above the K-edge of the element, the absorption probability therefore, scales with $Z^4$ through to $Z^6$. The exact factor in the exponent varies slightly from element to element. This means, in summary, that per unit mass, the X-ray absorption scales approximately with $Z^{3 \ to \ 4}$ and may be approximated by $Z^{3.5}$.

Compared to iodine, the following applies: barium is 1.2 times more radiopaque per unit weight; tantalum is 3.1 times more radiopaque per unit weight, platinum is 3.9 times more radiopaque per unit weight; and bismuth is 4.8 times more radiopaque per unit weight.

These are estimates. Since the X-ray absorption is the result of the sum of the X-ray absorption for the photoelectric effect, the Compton scattering and the Rayleigh scattering, the actual increase in the radiopacity is slightly lower.

If contrast materials are used which are more radiopaque, the recording of image datasets of identical image quality, defined by the contrast-to-noise ratio (CMR), requires less radiation. The reduction in X-ray radiation is proportional to the square of the corresponding increase in the contrast, the absorption probability, therefore.

Compared to iodine, the following applies: barium requires a dose that is less by a factor of 1.5 (32% dose reduction); tantalum requires a dose that is less by a factor of 9.4 (89% dose reduction); platinum requires a dose that is less by a factor of 15 (93% dose reduction); and bismuth requires a dose that is less by a factor of 23 (96% dose reduction).

These are also estimates, for which that stated above in this regard continues to apply.

By using heavier, more radiopaque contrast materials in embolization agents, it is therefore possible to achieve a significant improvement in the image quality with a constant radiation dose. Alternatively, a significant reduction in the radiation dose may be achieved while the same image quality is maintained. When the compatibility of the contrast materials with the human body is considered, tantalum, platinum, and gold appear to be the most promising contrast materials for use in the human body. In principle, any material from gadolinium to bismuth may be used if the biocompatibility is proven.

Ytterbium and holmium, which contain beta irradiator isotopes, may also be used for controlling buoyancy and radiopacity, with a stable isotope then being added as the contrast material. The radiopacity of these two metals is lower than that of tantalum and other elements having a higher atomic number, however.

However, such contrast materials having a high atomic number are first of all not suitable for a combination with multi-energy-computed tomography since the conventional dual-energy access is capable of separating a medium-heavy material, (e.g., iodine or barium), from lighter materials, (e.g., water and soft tissue), because different absorption properties exist. In particular, water and soft tissue absorb high- and low-energy X-rays substantially equally well while iodine absorbs lower energy X-rays much more than higher energy X-rays. This permits the use of lower energy X-rays in order to increase the visibility of iodine and of higher energy X-rays in order to improve the visibility of water and soft tissue. A good separation of these materials is possible by combining corresponding image datasets.

In contrast, materials having a high atomic number, (e.g., tantalum, platinum, gold, and bismuth), have increased X-ray absorption in the case of higher energies. This reduces the difference between the absorption behavior of high- and low-energy X-ray radiation. Contrast materials having a high atomic number cannot be effectively differentiated from soft tissue or comparable materials therefore if conventional dual-energy approaches are used.

The problem of imaging materials having a high atomic number, in particular an atomic number of at least 65, is that the k-edge of the contrast materials falls into the high-energy portion of the spectrum, so absorption in the case of higher energies of the X-ray radiation is increased. As a result, contrast materials having a high atomic number absorb X-rays of a low-energy spectrum and X-rays of a high-energy spectrum with approximately the same efficiency. This property impairs the visibility of the contrast materials having a high atomic number in the conventional dual-energy approach, which is ineffective, therefore.

One proposal for solving this problem was described in DE 10 2015 212 369 A1. This document describes an apparatus and a method for selective detection and quantification of contrast agents, wherein a multi-energy computer tomograph is embodied for recording two computed tomography scans of body material with different spectral distribution of the X-ray radiation. To detect and quantify contrast agent on the basis of nanoparticles, such as gold or iron, even in low concentrations, it is proposed that targeted k-edge imaging of heavy elements is enabled. For this, two X-ray spectra of a multi-energy computed tomography device are modified such that the one X-ray spectrum has substantially energy contributions below the k-edge of a heavy element, (e.g., gold or iron), the other X-ray spectrum has substantially energy contributions above this k-edge, for which a pre-filtering of the high energy X-ray spectrum, (e.g., with a tube voltage of 120 kV), by a tin pre-filter is proposed. X-ray photons with energies below the k-edge may thus be filtered out, so the average of the energies of the remaining photons lies above the k-edge.

The conventional approach using a low-energy X-ray spectrum, (e.g., at 90 kV tube voltage), and a high-energy X-ray spectrum, (e.g., at 120 kV tube voltage), using strong filtering by a tin filter, a filter with a mean atomic number is proposed. Some problems occur in this case, however. The adjustment of the X-ray spectra to the contrast material is not exact there because the spectra in all energy ranges are extremely different, they have great breadth, therefore. This makes it difficult to ascertain the material information by way of image processing, in particular combination, of the image datasets. In addition, a low X-ray beam intensity exists for the low-energy spectrum, which is generated with a low tube voltage. This results in a high radiation dose for the patient.

Added to this is the fact that the low-energy X-rays energy cannot efficiently penetrate fatter patients. In such cases, the detector dose is reduced, and the noise level increases significantly, therefore. In order to avoid this problem, the pulse width may be adjusted for the low-energy images. Added to this is the fact that the automatic dose control defines the low detector dose and automatically increases the tube voltage. This results in a further reduction in the quality of the dual-energy imaging since the spectral properties are unstable and the difference in energy between the X-ray spectra is reduced. When using an X-ray facility with a C-arm, the instability of the tube voltage during the rotation of the C-arm is highly likely to totally destroy the diagnostic value of the dual-energy imaging.

A comparable set of problems with intensity limitation also results for the high-energy spectrum, however. To raise the high-energy spectrum above the K-edge of tantalum, a significant thickness of the tin filter has to be used. This considerably reduces the X-ray intensity. This problem is intensified for materials having a high atomic number, (e.g., tungsten, platinum, iridium, or gold), which are customary materials for contrast markers in surgical instruments for angiography, (e.g., for stents, guide wires, and the like).

SUMMARY AND DESCRIPTION

The disclosure is therefore based on the object of disclosing high-quality dual-energy X-ray imaging, in particular dual-energy CT, which may be easily interpreted for contrast materials with a very high atomic number.

This object is achieved by the method, the X-ray facility, the treatment system, the computer program, and the electronically readable data carrier as disclosed herein. The scope of the present disclosure is defined solely by the appended claims and is not affected to any degree by the statements within this summary. The present embodiments may obviate one or more of the drawbacks or limitations in the related art.

In a method for multi-energy X-ray imaging of the type mentioned in the introduction, it is provided that the X-ray spectra are generated by using at least one spectrally acting filter, starting from a source spectrum of an X-ray source MARKER in such a way that the value of their differential spectrum has a maximum, sharply delimited in particular at least at its lower edge, which includes a range, beginning at the k-edge of the contrast agent material, of higher absorption by the contrast material.

The disclosure therefore proposes, in particular starting from a shared, identical source spectrum, generating two X-ray spectra by way of filtering, which spectra differ at least substantially only in a range of a maximum of the differential spectrum in which a significant difference exists with regard to the absorption of the contrast material. This means, outside of the, (e.g., sharply delimited), maximum the X-ray spectra may be at least substantially identical. For example, the portion of the maximum of the differential spectrum may be at least 90%, or at least 95%. In other words, at least 90% or at least 95% of the spectral portions may exist in the maximum. In addition, the maximum may be narrow, so the breadth of the maximum is, for example, 5 to 30 keV. It is basically conceivable to start from different source spectra for the respective X-ray spectra, although an embodiment that is easy to implement may provide that the same source spectrum is used for the two X-ray spectra with further advantages, as will be explained.

To achieve the maximum separation of other materials, for example, in the case of a patient of soft tissue and/or water, from the contrast material in dual-energy X-ray imaging, in particular dual-energy computed tomography therefore, two X-ray spectra generated from the same source spectrum of the X-ray source, with the same tube voltage therefore, may be produced with the aid of at least one filter of a filtering facility, which outside of a maximum range are at least substantially identical and thus generate substantially identical images outside of the spectral maximum range. The extremely high absorption by the contrast material exists inside of the maximum range, however, and this is provided for one of the X-ray spectra but is not provided for the other or is provided to a lesser extent. In particular, a dual-energy subtraction which may be advantageously carried out (in particular, as is customary with dual-energy imaging, as a subtraction of the logarithms, optionally provided with a factor, of the image intensities) for the ascertainment of the material information, once other proportions are increasingly subtracted out, thus results in primarily the portion of the contrast material remaining, optimum separation of image elements is provided therefore, which have different X-ray absorption properties. This is the case, however, since within the maximum the absorption properties of the contrast material and the other materials deviate from each other most strongly owing to the encompassed k-edge and the highly absorbing range adjoining it. In other words, the contrast material has an increased absorption probability owing to its k-edge.

While previous dual-energy imaging approaches to the visualization of contrast materials having a high atomic number tended to be unsuitable therefore, the present disclosure provides a smart approach for avoiding the problem of similarly high absorption in the range of high and low energies in that a filtering concept specifically developed for the visualization of contrast materials having a high atomic number is used. X-ray spectra are generated, which, in particular when the same source spectrum is used, have at least almost identical spectral ranges outside of the maximum. These at least almost identical spectral ranges therefore supply at least substantially identical image contents in dual-energy recording processes independently of the absorption properties of the contrast material and other materials that are present, for example of the human body. Dual-energy subtraction in respect of these portions of the image datasets supply almost no or minimal variations in intensity, in the case of a field of view of the human body, no or minimal anatomical background. The spectral ranges in which the X-ray spectra are substantially identical may also be referred to as "inactive" spectral ranges because they are selected such that the absorption probability of the contrast material is low there anyway. It would be ineffective anyway therefore to use these inactive spectral ranges for imaging.

On the other hand, an "active" spectral range exists in the range of the maximum, for which range a significantly higher intensity of the X-ray radiation is provided in at least one of the X-ray spectra. This maximum range or "active" spectral range was purposefully selected such that the absorption of the contrast material is much greater owing to the presence of the k-edge. In the example of tantalum as the contrast material, the absorption is greater by about the 4.3 times, and in the example of platinum as the contrast material, the adsorption is greater by about 4.1 times. These are estimates based on the photoelectrical absorption.

By starting from, in particular, the same source spectrum and smart selection of the at least one filter, which will be discussed in more detail below, the present disclosure allows narrow differential spectra to be provided, which are configured to the highly absorbing range of a respective contrast material. The maximum of the differential spectrum is at least substantially different from zero only in the maximum range, which includes the highly absorbing range above of the k-edge of the contrast material. The absorption probability of the contrast material is maximal here, in particular much higher than the absorption probability of other materials, for example, of soft tissue and/or water. The dual-energy subtraction will therefore offer maximum contrast material contrast and minimum contrast with regard to other materials.

Where broad spectra having a poor overlap outside of the range with high absorption, in particular below the k-edge, were used in the prior art therefore, the present disclosure uses a narrow differential spectrum having an outstanding overlap of the "inactive" spectral ranges below the k-edge or above the highly absorbing range of the contrast material. Because the same tube voltage may be used for both X-ray spectra, owing to the use of the same source spectrum, low tube voltages are not necessary, and no problems occur in respect of low X-ray intensities. Both X-ray spectra may be taken to mean high-energy X-ray spectra within the context of the present disclosure. The necessary patient dose may be reduced because, although the filtered X-ray spectrum (in particular by the contrast material itself or a material having an even higher atomic number, as explained below) still includes low-energy X-ray radiation it has fewer lowest-energy components than conventional dual-energy spectra, which contribute the most to the patient dose. While these components may also be filtered out in traditional dual-energy imaging, the intensity is then not adequate.

In an embodiment, the contrast material is used as a first filter material of a first of the at least one filter. Use of the contrast material itself as the first filter material for one of the at least one filter has the massive advantage that the lower edge of the maximum matches the k-edge of the contrast material and a particularly sharp delimitation of the maximum in the differential spectrum is achieved. While it is basically conceivable to use the second X-ray spectrum spectrally unfiltered, a filter material having a higher atomic number than the contrast material may be used particularly advantageously as the second filter material of second filter for the second X-ray spectrum. This means that to obtain a particularly sharply delimited maximum and thus a sharply delimited "active" spectral range, the k-edge of a further material, namely of the second filter material, having a high atomic number may be utilized since the k-edge thereof naturally lies at a higher energy level than the k-edge of the contrast material and first filter material.

If different filters are used for the two X-ray spectra therefore, namely a first filter made of the contrast material for the first X-ray spectrum and a second filter made of a second filter material having a higher atomic number than the contrast material for the second filter and thus the second X-ray spectrum, a differential spectrum results, which has the clearly defined, narrowband maximum in the range between the two k-edges and outside is at least substantially zero because the filter properties are at least substantially identical. In other words, the maximum of the differential spectrum and thus the "active" spectral range begins at the k-edge of the contrast material and extends, covering the highly absorbing range of the contrast material above the k-edge, to the k-edge of the second filter material. The second filter material may be selected, for example, such that the interval of the k-edge of the second filter material from that of the contrast material is 5 to 40 keV, so the desired narrow band nature of the differential spectrum is provided.

If, for example, tantalum (atomic number 73), platinum (atomic number 78), or gold (atomic number 79) is considered as the contrast material and used as the first filter material, then lead (atomic number 82) or bismuth (atomic number 83) may be used as the second filter material. In one example, lead is used as an inexpensive solution. Should the contrast material be holmium or ytterbium (atomic numbers 67 and 70), then tantalum (atomic number 73) may be used as the second filter material. The corresponding k-edges lie at 55.62 keV for holmium, at 61.33 keV for ytterbium, at 67.43 keV for tantalum, at 78.40 keV for platinum, at 80.73 keV, at 88.00 keV for lead, and at 90.54 keV for bismuth.

If the contrast material is, for example, tantalum, a tantalum filter may be used as the first filter and a lead filter or bismuth filter may be used as the second filter. These filters generate at least substantially identical X-ray spectra at energy levels below 67.43 keV and above 88.00 or 90.54 keV. These two "inactive" spectral ranges thus supply substantially identical image data. The dual-energy subtraction of these image portions is substantially free of content, independently of the absorption properties of the recorded materials.

However, the tantalum-filtered and bismuth-filtered X-ray spectra differ significantly in the ("active") spectral range and therefore also maximum range of 67.43 keV through to 90.54 keV, which extends from 67.43 keV to 88.00 keV when lead is used instead of bismuth. In this spectral range, the subtracted image datasets exhibit maximum separation of the image elements if they have different X-ray absorption properties. In this spectral range, the absorption properties of tantalum and other materials, customarily found in the field of view, may be most clearly differentiated from tantalum owing to the k-edge. The dual-energy recording process is thus highly sensitive to the image content of the tantalum owing to the specific properties of the tantalum-filtered and bismuth-filtered or lead-filtered X-ray spectra, so the distribution of the tantalum as the contrast material may be identified in high quality and contrasts of other materials may be suppressed.

The display information, in particular when using the two filter as described, may be ascertained by dual-energy subtraction of the image datasets. It is expedient, moreover, if the display information is ascertained as a display image showing the distribution of the contrast material, in particular together with a further display image, which displays the other materials. In particular, a joint display and/or further processing of the display image and of the further display image may then take place, for example, to check a positioning of the contrast material or of an agent containing it. A density image of the contrast material may also be ascertained as an, optionally further, display image. In the individual application of embolization, such a density image also describes the density of the embolization agent, so it is possible, in particular, to make improved statements on the clinical effect of the embolization.

In certain examples, access may be simplified in that only a dedicated filter, namely the filter including the contrast material itself, is used, it being possible for the second X-ray spectrum to remain unfiltered or to only be filtered by standard copper filters, which would then have to be provided for both X-ray spectra. It should also be noted at this point that the access described here should of course be applied to spectrally modifying filters, so of course other filters may be present, for example, form filters. However, it is expedient to use these filters identically for both X-ray spectra too.

While the present disclosure may also be applied in material testing tasks and the like outside of medical problems, it has particular suitability with regard to the use of contrast materials and contrast agents inside the human body, in particular for examination and/or treatment purposes. A particular field of application of the present disclosure may be found in embolization procedures in the target area of a patient in which an embolization agent containing the contrast agent is used, for example, microparticles containing the contrast material.

The present disclosure therefore also relates, in particular, to a method for imaging after an embolization procedure using an embolization agent, in particular microparticles, including a contrast material, which has an atomic number of at least 65, in particular at least 73, and/or a k-edge of at least 60 keV in a field of view of patient, with a multi-energy X-ray imaging method as described above being used for ascertaining display information of the contrast material. Computed tomography (CT) may be used, in particular what is known as C-arm CT, which may be implemented in the procedure room with an X-ray facility having a C-arm.

As in the treatment system still to be discussed as well, a combination of very heavy, metallic, radiopaque additives having a high atomic number, of the contrast material, therefore, is therefore particularly advantageously proposed, as described above, in embolization agents having the specific filter concept for dual-energy X-ray imaging. In particular, the embolization agent may be microparticles, which also include an active ingredient. For example, the embolization agent may be implemented as what are known as radio embolization pearls. If the compatibility of contrast materials with the human body, the biocompatibility therefore, is considered, in particular tantalum, platinum and gold present themselves as contrast materials for embolization agents. In principle other material, in particular material having atomic numbers from tantalum to bismuth, may also be used, however, if biocompatibility is given. In certain exemplary embodiments, stable isotopes of ytterbium and holmium may also be considered. Specifically, as described in the introduction, the portion of contrast material in the embolization agent may be selected here to minimize the buoyancy in the blood or in another carrier fluid, with it being possible for the carrier fluid to be, for example, saline solution and/or a contrast agent based on a different contrast material, in particular iodine.

In a corresponding treatment system, this kind of use of materials having a high atomic number as the contrast material in the embolization agent, in particular microparticles, is supplemented by an X-ray facility, which has the corresponding at least one filter in order to carry out the multi-energy-computed tomography imaging method. A control facility may be embodied to actuate the components of the X-ray facility to implement the multi-energy computed tomography imaging method. This provides dedicated X-ray filtering, which significantly improves the visibility of the contrast material and thus of the embolization agent. In the present case, there should only be other materials in the field of view, which change their absorption properties between the two generated X-ray spectra significantly less than the contrast material. The other materials in the field of view will customarily be normal anatomic materials, for example, soft tissue and/or water as well as other anatomic materials. It should be stressed, however, that a clear distinction of the contrast material from other contrast agents used, for example, iodine-containing contrast agents, is also possible because, for example, iodine in the "active" spectral range covered by the maximum does not have a k-edge, so the visibility of embolization agents in the presence of iodine-containing or other contrast agents is also intensified. Simultaneous suppression of soft tissue and iodine-containing contrast agents is possible, something which conventional dual-energy approaches are not capable of achieving.

As already mentioned, the embolization agent may include microparticles, in particular microbeads. It may also be provided in the treatment system that the embolization agent has at least one chemical and/or radioactive active ingredient for transarterial chemoembolization (TACE) and/or for selective internal radiation therapy (SIRT). Furthermore, the microparticles may have a plastic carrier material, for example, for forming hollow beads. Other forms for the microparticles, in which forms these microparticles are embodied so as to be hollow, are also conceivable, however. The active ingredient may then be arranged inside of the microparticles. As far as the contrast material is concerned, this may also be arranged inside the microparticles; alternatively or in addition it is also conceivable, however, to provide the contrast material as a coating of the microparticles.

A particularly advantageous treatment method of a patient may also be achieved by the treatment system and the imaging method after an embolization procedure.

A treatment method of this kind for treating a lesion in a target area of a patient, in particular using a treatment system, may include providing an embolization agent, which includes a chemical and/or radioactive active ingredient for transarterial chemoembolization (TACE) and/or for selective internal radiation therapy (SIRT) and a contrast material, which has an atomic number of at least 65, in particular at least 73, and/or a k-edge of at least 60 keV. The treatment method may further include introducing the embolization agent into a target area including the lesion to be treated, in particular in such a way that it accumulates on the lesion. The treatment method may further include monitoring and/or checking the positioning and/or density of the embolization agent by ascertaining display information of the contrast material by multi-energy X-ray imaging, in particular computed tomography imaging, of the field of view. In this process, two image datasets having different X-ray spectra are recorded and are combined to ascertain the display information of the contrast material. Additionally, the X-ray spectra are generated by using at least one spectrally acting filter starting from a, in particular the same, source spectrum of an X-ray source in such a way that the value of their differential spectrum has a maximum, sharply delimited in particular at least at its lower edge, which includes a range, beginning at the k-edge of the contrast material, of higher absorption by the contrast material.

Further embolization agents may then be introduced, for example, as a function of an evaluation of the display information of the contrast material. In particular, ascertaining a density of the contrast material as display information is expedient here. The measured density is proportional to the radiation dose of the surrounding tissue in the case of the SIRT or proportional to the density of the embedded chemotherapeutic agent in the case of TACE. All statements relating to the multi-energy X-ray imaging method, to the imaging method after an embolization procedure, and to the treatment system continue to apply accordingly to a treatment method of this kind.

When the contrast material may also be used for setting the buoyancy, further advantages are given by contrast materials having a high atomic number, as has already been discussed in the introduction. This is because such contrast materials offer much higher absorption per unit weight, in the example of tantalum approximately 3.1 times, and in the example of platinum approximately 3.9 times higher absorption. Dose reductions by approximately a factor of 4.9 and 15 respectively may be attained hereby. These are also estimated values.

Because it is possible to achieve not only a suppression of the anatomical background for the display information, (e.g., a display image produced by subtraction of the image datasets), but also a suppression of background generated by other contrast agents, (e.g., iodine-containing contrast agents), a particularly contrast-rich visualization of the radiopaque embolization agent, (e.g., of the microparticles), with less anatomical background and less background produced by iodine or comparable materials is possible. The combination of radiopaque embolization agents with contrast material having a high atomic number and dedicated filtering, in particular also materials having a higher atomic number, produces a unique embolization platform in which it is possible to benefit from the improved visibility of the embolization agent and the possibilities resulting therefrom for SIRT and TACE procedures. In particular, omission of SPECT imaging may be achieved with regard to the SIRT procedures. Monitoring and control of the embolization is much improved, in particular also with regard to the speed, because frequent relocating of the patient, in particular for SPECT scans, is not necessary. Fewer staff and less equipment is required and the nuclear medical facility, (e.g., SPECT/CT or PET/CT), may also be omitted. In particular, the disclosure also makes it possible to provide the display information during an embolization procedure, so corrections are conceivable and thus treatment is improved.

Use of the multi-energy X-ray imaging method in medical engineering is not confined to embolization procedures of this kind, however. Instead the same access with contrast materials having a high atomic number may also be used in other procedures in which contrast agent is used, so a method for imaging a contrast agent in a field of view is also conceivable, with the contrast agent including a contrast material, which has an atomic number of at least 65, in particular at least 73, and/or a k-edge of at least 60 keV, with a multi-energy X-ray imaging method being used to ascertain display information of the contrast material and thus of the contrast agent. This is extremely useful and relevant, in particular, for contrast agents based on nanoparticles, for example, contrast agents using gold nanoparticles. Furthermore, great potential also exists with regard to tungsten-based contrast agents. Two-dimensional imaging, radiography, and/or fluoroscopy may also take place in addition to computed tomography in this case.

The disclosure also relates to an X-ray facility, having a control facility embodied for carrying out at least one of the methods. This means the control facility, which may have at least one processor and/or at least one storage device or apparatus, is configured to carry out the multi-energy X-ray imaging method and optionally also the imaging method after embolization procedures and/or the imaging method for contrast agent. The X-ray facility therefore has a filtering facility having the at least one filter, which may be brought, in a manner controlled, in particular, by the control facility, selectively into the beam path of the X-ray radiation of at least one X-ray source of the X-ray facility. The X-ray facility, which is, in particular, a dedicated computed tomography facility and/or an X-ray facility having a C-arm, which is embodied for C-arm CT, may include exactly one X-ray source or else a plurality of X-ray sources. In the case of at least two X-ray sources, it is therefore possible to record the image datasets of the different X-ray spectra simultaneously in parallel, so movement artifacts and the like are avoided or reduced. A fundamental field of application here, in particular in the case of the X-ray facility having a C-arm, but also beyond this, is what is known as cone beam CT. Two-dimensional applications of the dual-energy X-ray imaging method may also be advantageously implemented, in particular in radiography and fluoroscopy, with an X-ray facility having a C-arm.

In certain examples, the filtering facility has the first filter made of the contrast material, and the second filter is made of the further material having a higher atomic number than the contrast material, wherein the filtering facility is configured to be brought, in a manner controlled by the control facility, selectively into the beam path of at least one X-ray source of the X-ray facility in order to record the first or the second image dataset with the corresponding first or second X-ray spectrum. For this, the control facility may actuate the X-ray source, in particular an X-ray tube, to provide the same source spectrum for both image datasets with the same tube voltage. The filtering facility may optionally also have further filters, (e.g., a copper pre-filter, a form filter, and the like).

In order to carry out the multi-energy X-ray imaging method, the control facility may have a recording unit. The recording unit is embodied for controlling the recording operation of the X-ray facility by actuating the corresponding components, therefore in particular also to actuate the at least one X-ray source and the filtering facility in order to achieve the corresponding X-ray spectra. The image datasets are recorded with at least one X-ray detector, it being possible to also provide two recording arrangements, including one X-ray source and one X-ray detector respectively, for a biplane X-ray facility having two X-ray sources by providing one X-ray detector for each of the X-ray sources, respectively. In addition to the recording unit, the control facility may also have a reconstruction unit for reconstruction of the image datasets from the projection images and an ascertaining unit for ascertaining the display information from the image datasets.

The treatment system that has already been discussed includes an X-ray facility and embolization agents, in particular microparticles, with the embolization agent including a contrast material, which has an atomic number of at least 65, in particular at least 73, and/or a k-edge of at least 60 keV. In certain examples, the X-ray facility may expediently have a display facility for displaying the display information, in particular a contrast material image of the display information.

A computer program may be directly loaded into a control facility of an X-ray facility and has program means in order to carry out the acts of a method, in particular also by appropriate actuation of a filtering facility of the X-ray facility. The computer program may be stored in an electronically readable data carrier, which therefore includes control information stored thereon, which includes at least one computer program and when the data carrier is used in a control facility of an X-ray facility equips it to carry out a method.

The data carrier may be a non-transient data carrier, for example, a CD-ROM.

BRIEF DESCRIPTION OF THE DRAWINGS

Further advantages and details of the present disclosure may be found in the exemplary embodiments described below and with reference to the drawings. In the drawings.

DETAILED DESCRIPTION

Figure 1:
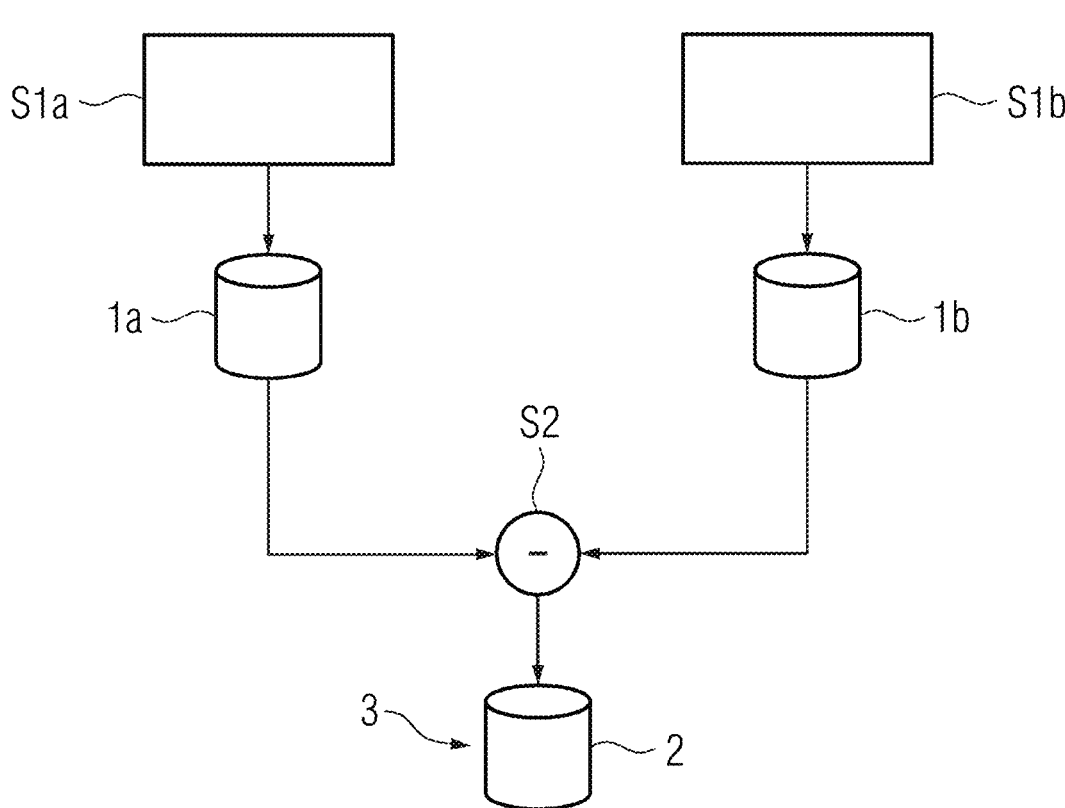
FIG. 1 depicts a flowchart of an exemplary embodiment of a multi-energy X-ray imaging method.

FIG. 1 shows a flowchart of exemplary embodiments of the method, which are used for multi-energy X-ray imaging of a contrast material in a field of view, in particular of a patient. While the present disclosure may also be used for situations other than medical-technical ones, the exemplary case of a field of view belonging to a human body shall be considered below. In the present case, computed tomography methods are explained by way of example, although 2D-applications are also conceivable.

The contrast material may have an atomic number of at least 65, in particular at least 73, and/or a k-edge of at least 60 keV. In the medical-technical individual application, contrast materials of this kind having a very high atomic number, in particular metals, are customarily administered for the purpose of improved contrast of the administered entire complex, of which they form a part. For example, it may be a contrast agent, in particular for improved visualization of blood vessels. In particular, the contrast material, as gold nanoparticles, may then form part of the contrast agent and/or it may be a contrast agent based on tungsten. A primary individual application of the present disclosure, for which particular advantages are achieved, is, however, the use of the contrast material in an embolization agent, in particular microparticles, which may include, for example, a hollow plastic carrier material inside of which an active ingredient is arranged. The contrast material may then likewise be provided inside the microparticles but also as a coating thereof.

In the representation of FIG. 1, image datasets 1a and 1b respectively of the field of view are recorded in acts S1a and S1b using different X-ray spectra. In particular when a biplane computed tomography facility is used, it is possible to execute the acts S1a and S1b simultaneously in parallel to reduce movement artifacts and the like.

The two different X-ray spectra are obtained, starting from the same source spectrum of an X-ray source, by filtering by at least one filter of a filtering facility. In the present exemplary embodiment, the filtering facility includes a first filter for generating the first X-ray spectrum from the source spectrum and a second filter for generating the second X-ray spectrum from the source spectrum. The contrast material is used as a first filter material of the first filter; a material having a higher atomic number than the contrast material is used as the second filter material of the second filter. This produces two X-ray spectra, which, apart from the range between the two k-edges of the two filter materials, are at least substantially identical. This means their difference is almost zero. Between the k-edge of the first filter material, of the contrast material therefore, and the k-edge of the second filter material there exist significant differences between the two X-ray spectra, however, so a maximum exists there in the differential spectrum. Owing to the use of the contrast material as the first filter material this maximum, which begins here at the k-edge of the contrast material, contains as an "active" spectral range the range of extremely high absorption by the contrast material, which follows above the k-edge. The maximum is sharply delimited, moreover, owing to the k-edges. The second filter material may be selected, for example, in such a way that its k-edge determining the width of the maximum is 5 keV to 30 keV removed from the k-edge of the contrast material.

Outside of the maximum, with lower X-ray energies than the k-edge of the contrast material and higher X-ray energies than the k-edge of the second filter material therefore, the X-ray spectra are substantially identical, so this spectral range may also be referred to as an "inactive" spectral range. For example, at least 90% or at least 95% of the spectral portions of the differential spectrum may lie within the maximum.

The following applies to these "inactive" spectral ranges, however. When the image datasets 1a and 1b are subtracted from each other these image portions cease to be independently of the absorption properties of the recorded materials. In medical-technical applications, the anatomical background, as well as other contrast agent used, in particular containing iodine, during a subtraction, as is also provided in act S2, is faded out hereby. Since the significant difference between the two X-ray spectra in the energy range of the maximum lies between the two k-edges, in the "active" spectral range therefore, the subtracted image datasets 1a, 1b, in a display image 2 obtained as display information 3, supply the distribution of the contrast material in this case, while soft tissue contrasts, water contrasts and other contrasts, for example iodine contrasts, are suppressed. As the term "contrast material" expresses, there are no further materials present in the field of view whose k-edge falls in the range of the maximum, lie between the k-edges of the contrast material and of the second filter material, therefore.

Apart from the subtraction, act S2 may also contain further processing acts to emphasize the different absorption properties in the active spectral range of the maximum for the contrast material even more clearly and to obtain an even higher-quality display image 2. In particular, when X-ray spectra that are not filtered by two materials having a high atomic number are used, and instead other X-ray spectra, which in their differential spectrum form a maximum in the high absorption range of the contrast material starting from the k-edge, are used, other methods of material breakdown may also be used to obtain the display information 3, in particular the display image 2. Of course, it is also possible to ascertain, in addition to the display image 2, a further display image, which then shows the other materials, in particular the soft tissue and/or other anatomical features. The display information 3 and optionally the further display image may be output accordingly, optionally also overlaid with a particular emphasis of the contrast material or the like.

Figure 2:
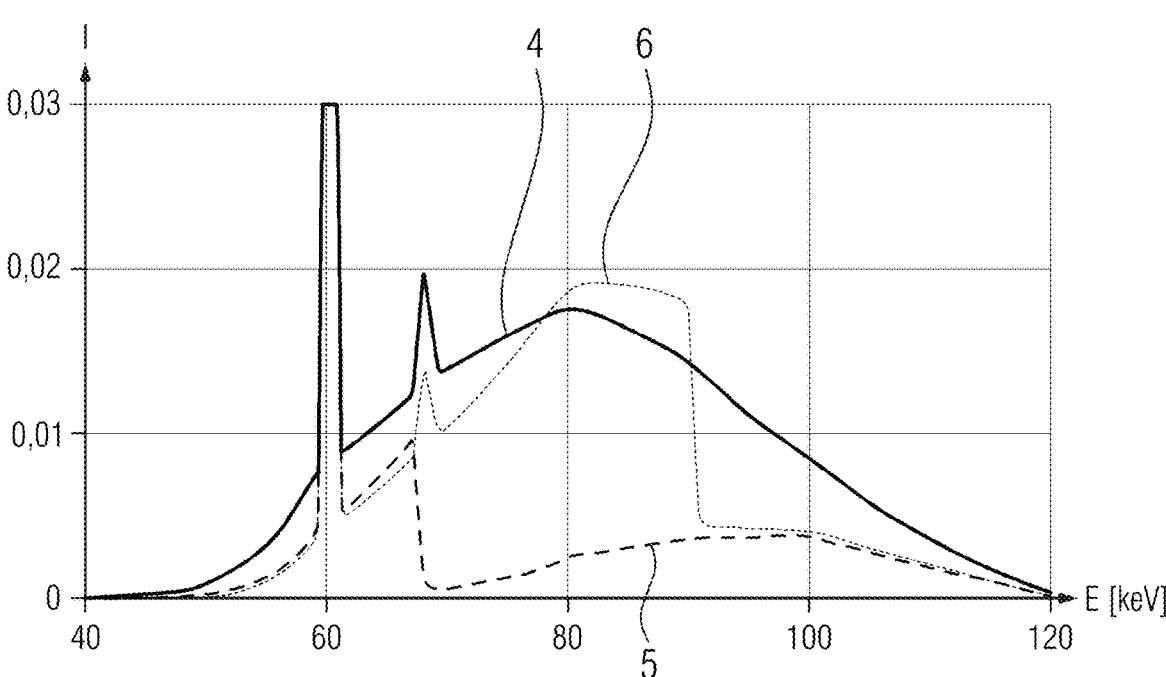
FIG. 2 depicts an example of X-ray spectra for separation of tantalum as the contrast material from other image contents.

This shall now be explained in more detail using some specific examples. In a first example, tantalum is used as the contrast material and bismuth as the second filter material. In this regard, FIG. 2 shows different spectra of X-ray radiation as X-ray radiation intensity I in arbitrary units plotted against the X-ray energy E in keV. Firstly, the characteristic curve 4 of the unfiltered source spectrum may be seen, together with the characteristic curve 5 of the first X-ray spectrum (filtered by the contrast material) and the characteristic curve 6 of the second X-ray spectrum (filtered by the second filter material, in this case, bismuth). It is apparent that, up to the k-edge of tantalum, which lies at approximately 67.43 keV, the two spectra 5, 6 proceed at least substantially identically, after which, owing to the high absorption that begins there, the intensities of the first X-ray spectrum, characteristic curve 5, decrease significantly. The intensities of the second X-ray spectrum, characteristic curve 6, remain high, at approximately 90.54 keV, up to the k-edge of bismuth, however, until there too a drop occurs and above this X-ray energy the spectra proceed substantially identically again.

Figure 3:
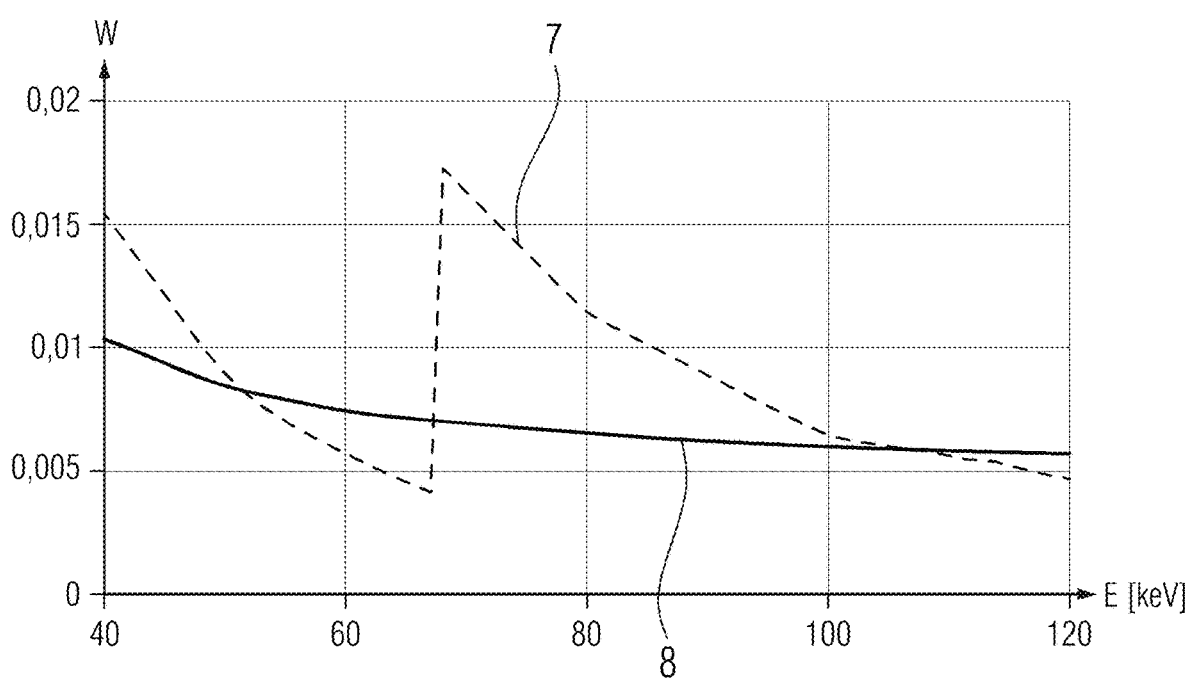
FIG. 3 depicts an example of absorption probabilities plotted against X-ray energies for tantalum and soft tissue.

By way of further explanation, FIG. 3 shows the absorption probability W in arbitrary units, likewise plotted against the X-ray energy E in keV for tantalum (characteristic curve 7) and soft tissue (characteristic curve 8). It may be seen that at the k-edge of tantalum there is a jump to a much higher absorption while the absorption of soft tissue remains substantially the same over the range of the X-ray spectra.

Figure 4:
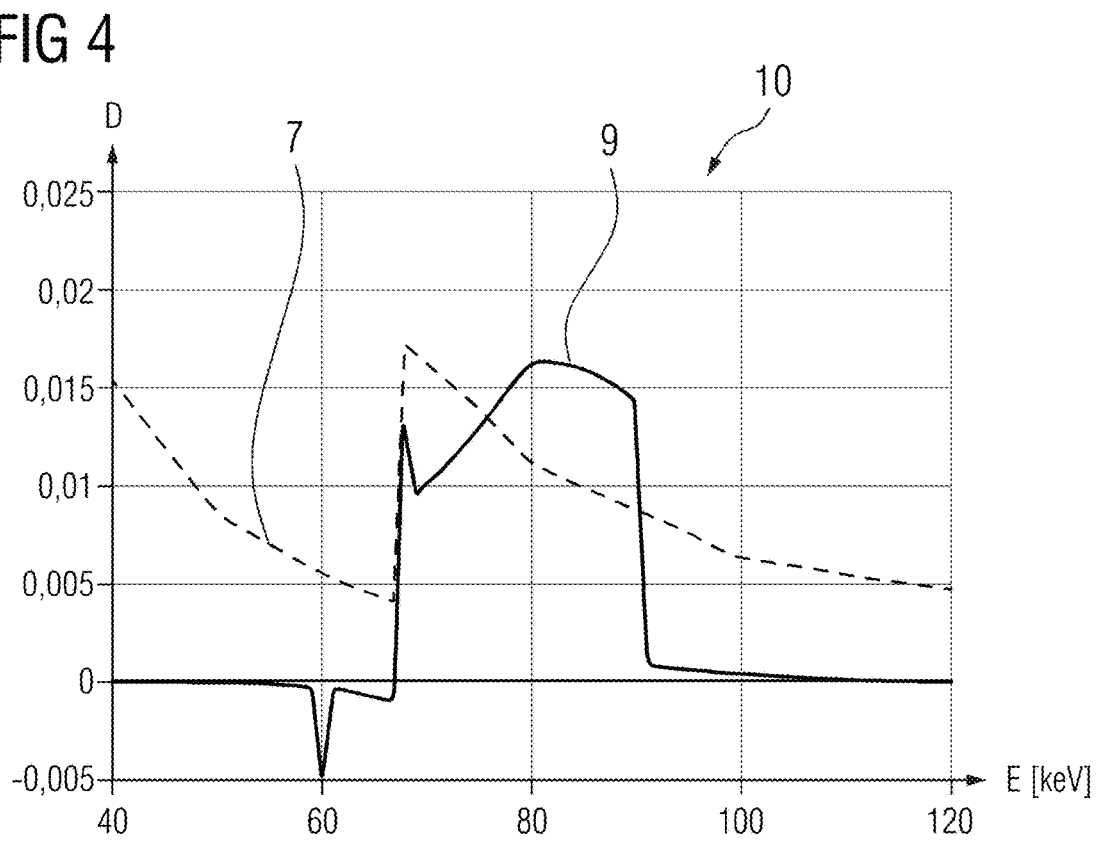
FIG. 4 depicts the differential spectrum of the filtered X-ray spectra of FIG. 2 together with the absorption probability of tantalum.

FIG. 4 shows the differential spectrum of the two X-ray spectra, the characteristic curves 5 and 6 therefore, as characteristic curve 9. It is apparent that a significant maximum occurs in the "active" spectral range between the two k-edges, while the differences are otherwise minimal and lie at almost zero. Shown overlaid once again is the characteristic curve 7 of the absorption of tantalum from which the emphasis of the massive differences in absorption, precisely in the range of the maximum 10, clearly results.

Figure 5:
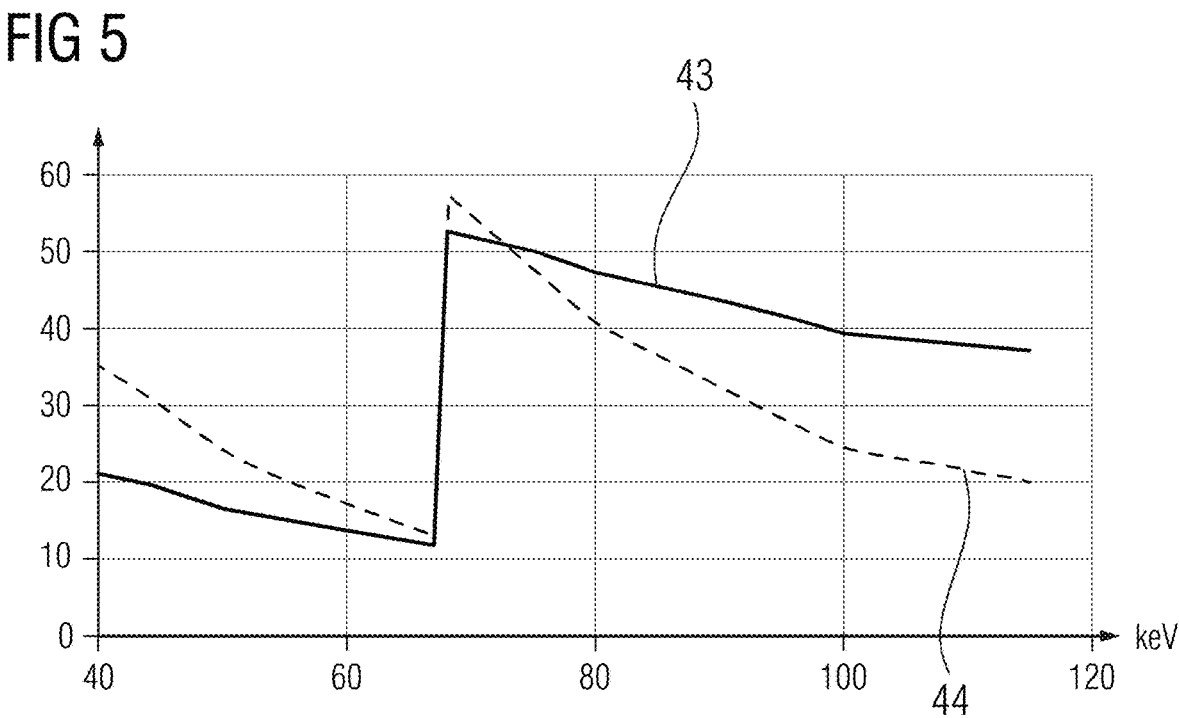
FIG. 5 depicts an example of ratios of the absorption probability of tantalum to iodine and tantalum to human soft tissue.

FIG. 5 shows firstly the ratio of the absorption probabilities of tantalum to iodine (characteristic curve 43) and secondly the ratio of the absorption probabilities of tantalum to tissue (characteristic curve 44) plotted against the energy. It may clearly be seen that the characteristic curves 43 and 44 in the "inactive" spectral range are less similar but are more similar in the "active" spectral range. For this reason, it is possible to suppress iodine and soft tissue but retain and measure the signal of the tantalum.

Figure 6:
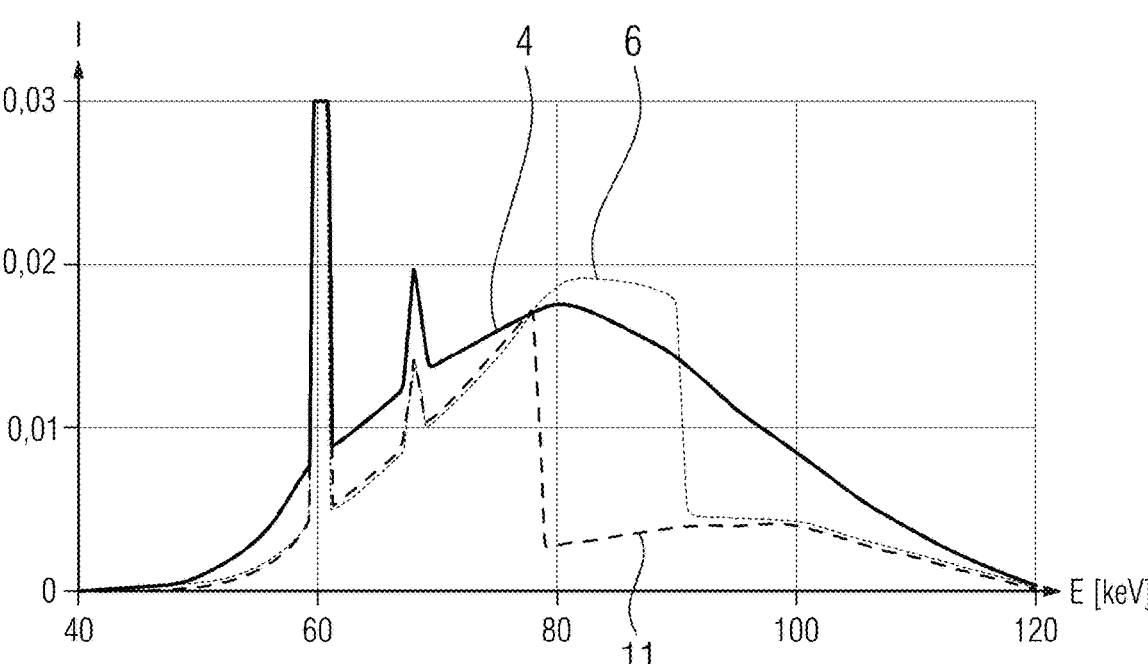
FIG. 6 depicts an example of X-ray spectra for the improved display of platinum as the contrast material.
Figure 7:
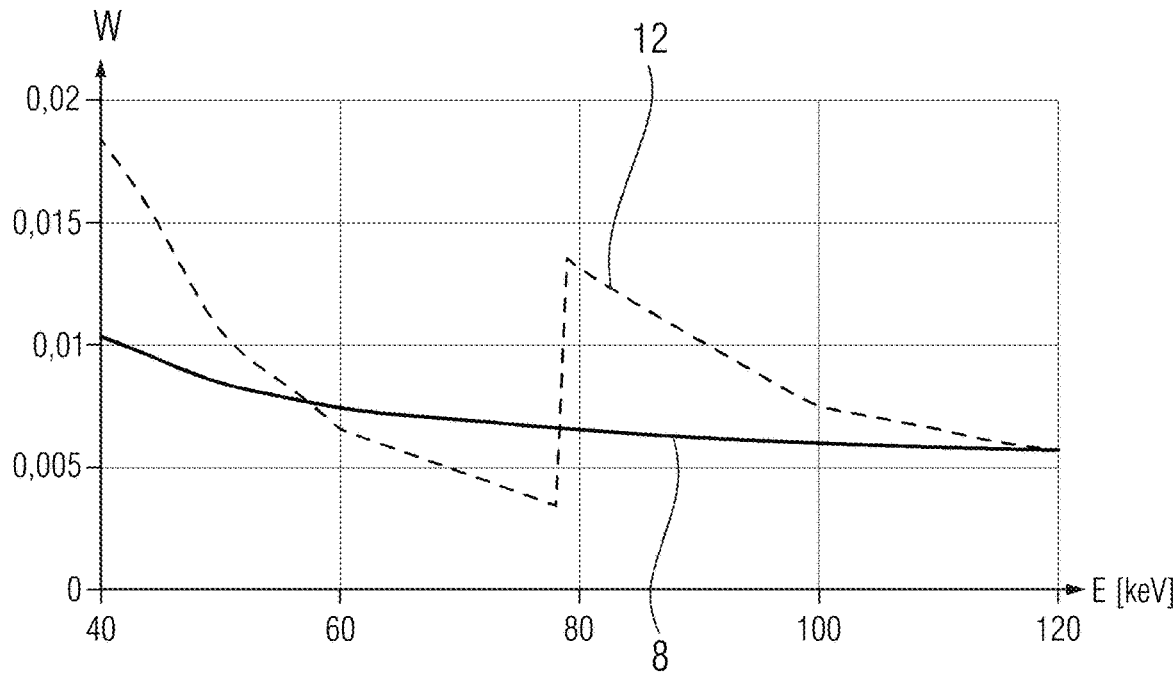
FIG. 7 depicts an example of absorption probabilities for platinum and soft tissue.

FIGS. 6 and 7 analogously explain a further exemplary embodiment, with platinum being used here as the contrast material and bismuth again being used as the second filter material. The k-edge of platinum lies at approximately 78.40 keV, so here the "active" spectral range, as may be seen from the characteristic curve 11 for the platinum-filtered first X-ray spectrum, is slightly narrower, specifically it lies between 78.40 keV and 90.54 keV. As FIG. 7, which is analogous to FIG. 3, shows, the absorption behavior of platinum, displayed by the characteristic curve 12, exhibits a highly absorbing range exactly within the range of the maximum 10 which results here.

In these two first specific examples, a 120 keV spectrum generated with a tube voltage of 120 kV may be used as the source spectrum with high-energy source spectra, in particular in the range of 110 to 140 keV as the maximum energies being possible, because low-energy spectra may then be completely dispensed with, and a good contrast is provided at a low dose.

Figure 8:
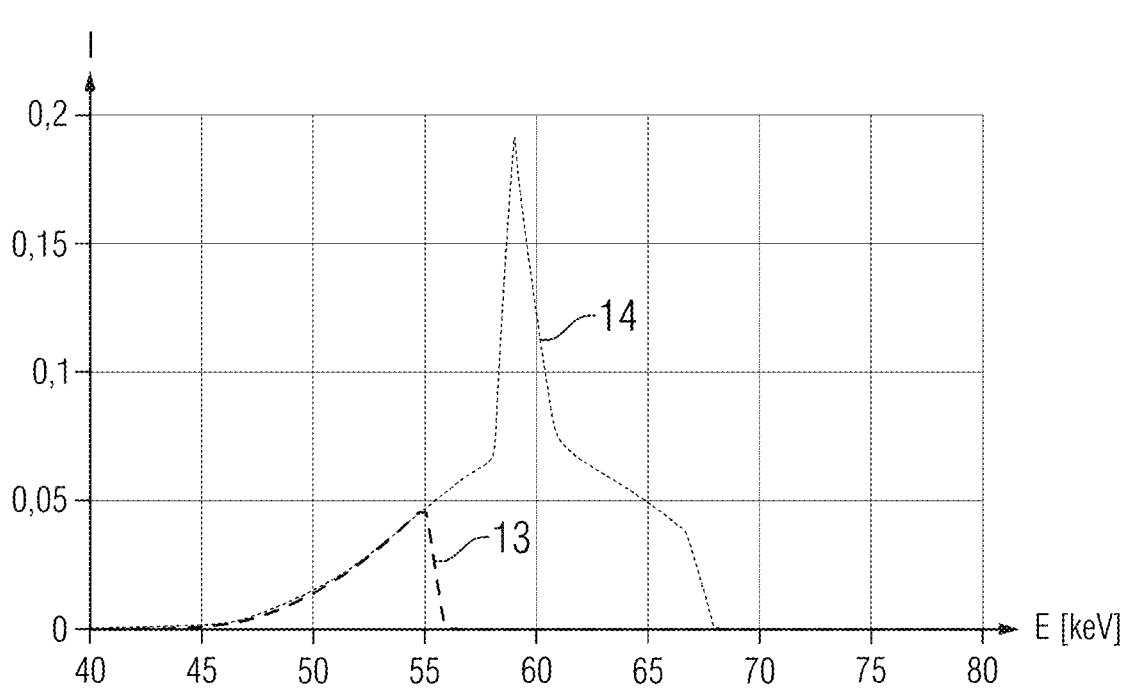
FIG. 8 depicts an example of X-ray spectra when holmium is used as the contrast material.

Exemplary embodiments are also conceivable, however, in which contrast materials having a lower atomic number than tantalum are used, such as the example of FIG. 8 shows in which holmium (k-edge at 55.62 keV) is used as the contrast material and tantalum as the second filter material. For the sake of simplicity, only the characteristic curves 13, 14 of the respective filtered X-ray spectra are shown, it being possible to also use a low-energy spectrum here as the source spectrum.

Owing to the properties of the two X-ray spectra specifically coordinated with the contrast material, the dual-energy acquisition, as described here, is highly sensitive to the contrast material in the field of view and may thus render the distribution of the contrast material in the field of view eminently visible.

The multi-energy computed tomography imaging method described here may be advantageously used in different medical contexts, for example, when a contrast agent using the contrast material is used, in a corresponding method for imaging the contrast agent, but particularly in a method for checking the accumulation of a previously administered embolization agent, which contains the contrast material.

Figure 9:
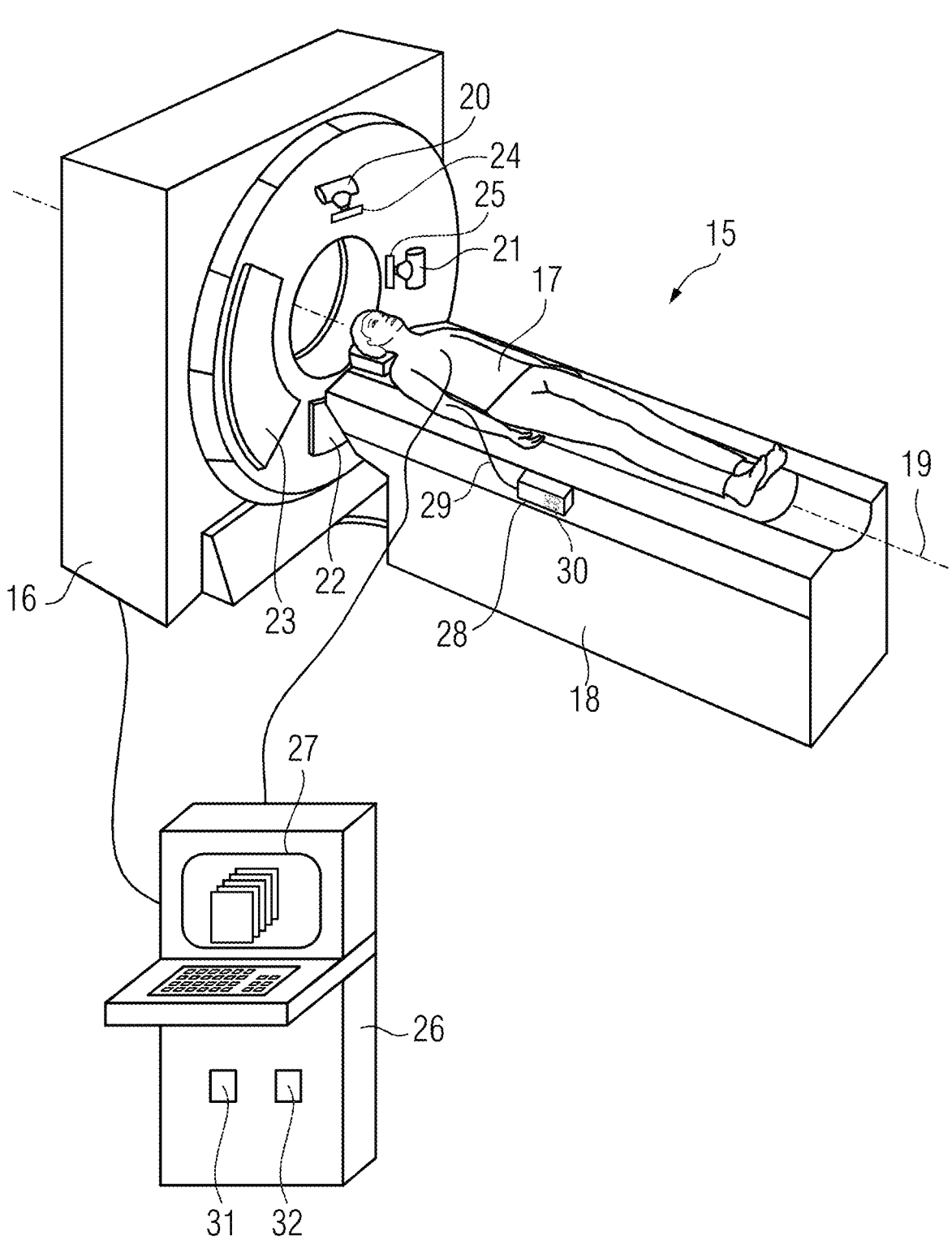
FIG. 9 depicts an X-ray facility according to a first exemplary embodiment.

FIG. 9 shows a schematic sketch of an X-ray facility 15, here a biplane computed tomography facility. The X-ray facility 15 includes, as is basically known, a gantry 16, which has a central opening into which a patient 17 may be moved by a patient table 18.

Provided in the gantry 16, mounted about an axis of rotation 19, are two recording arrangements, which include X-ray sources 20, 21 and associated X-ray detectors 22, 23, respectively. Filtering facilities 24, 25 are connected downstream of the X-ray sources 20, 21, respectively.

Operation of the X-ray facility 15 is controlled by a control facility 26, shown schematically externally here, which in the present case also has a display facility 27 on which the display information 3, in particular the display image 2, may be output.

Also indicated in FIG. 9 is a treatment facility 28, which may have, for example, an embolization catheter 29 (only hinted at) in order to administer embolization agent 30 (likewise only hinted at) to a patient 17 in the field of view.

Because the control facility 26 is embodied for carrying out the method, in particular as described in FIG. 1, and the embolization agent 30 contains contrast material, (e.g., tantalum, platinum, or gold), the X-ray facility 15 and the embolization agent 30, optionally together with the treatment facility 28, form a treatment system for carrying out embolization procedures. Here the embolization agent 30 and the X-ray facility 15 are coordinated with each other in the sense that the filtering facilities 24, 25 may have a filter made of the contrast material, which may be introduced, in particular selectively, into the beam path, controlled by the control facility 26, and a filter made of a second filter material having a higher atomic number, for example made of bismuth, which may be brought selectively into the beam path, likewise controlled by the control facility 26, and in addition the control facility 26 is embodied for carrying out the multi-energy computed tomography imaging method, as described in relation to FIG. 1. Due to the two recording arrangements, the control facility 26 may simultaneously generate, for example, the two X-ray spectra in that the respective X-ray sources 20, 21 are actuated with the same tube voltage to generate the same source spectrum, but in the filtering facility 24, for example, the first filter made of contrast material and in the filtering facility 25 the second filter made of the second filter material is used, so the two X-ray spectra are produced simultaneously. Rotating the recording arrangements about the field of view of the patient 17 simultaneously generates projection images by both recording arrangements, although with the different X-ray spectra, so the image datasets 1a and 1b are produced after reconstruction. All of this may take place controlled by a recording unit 31 of the control facility 26, by which acts S1a and S1b are carried out, therefore. The display information 3 may then be ascertained in an ascertaining unit 32 according to act S2.

A treatment system for carrying out an embolization procedure therefore supplies components that are perfectly coordinated with each other for high-quality imaging, which show the accumulation of the embolization agent 30 with high contrast and in high quality, in particular also high spatial resolution, even in the case of small quantities.

The filtering facilities 24, 25 may also contain further part filters, (e.g., form filters and/or shared pre-filters), for example, made of copper, which should be selected to be identical, however, likewise for generating the image datasets 1a and 1b, so the sole difference is produced by the different first and second filters made of the contrast material or the second filter material. This provides that the two X-ray spectra outside of the range between the two k-edges ("active" spectral range) are as identical as possible.

Figure 10:
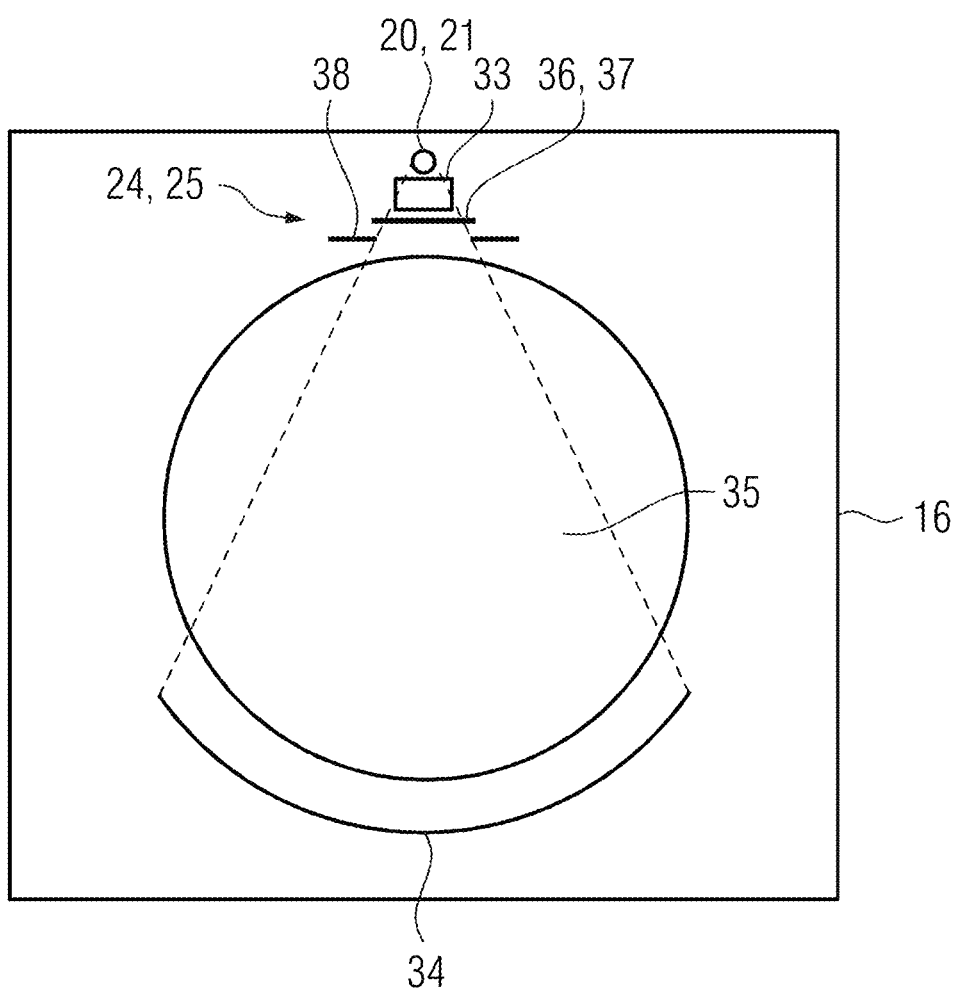
FIG. 10 depicts a schematic representation of an example of an X-ray source having a filtering facility.

FIG. 10 schematically shows, for the sake of clarity only for one of the X-ray sources 20, 21, the embodiment of the corresponding filtering facility 24, 25 in more detail. The filtering facilities 24, 25 accordingly firstly include a form filter 33, which in the present case provides a cone beam geometry of the resultant X-ray radiation field 34 in the opening for the patient 35. After the form filter 33, a spectral modification takes place according to the first filter 36 or the second filter 37 respectively depending on whether the first image dataset 1a or the second image dataset 1b is to be recorded using this X-ray source 20, 21. The first filter 36 is made of the contrast material, the second filter 37 of the second filter material, for example, bismuth. The radiation field 34 is suitably delimited by diaphragms 38 and is directed onto the associated detector 22, 23 (not shown here).

Figures 11, 12:
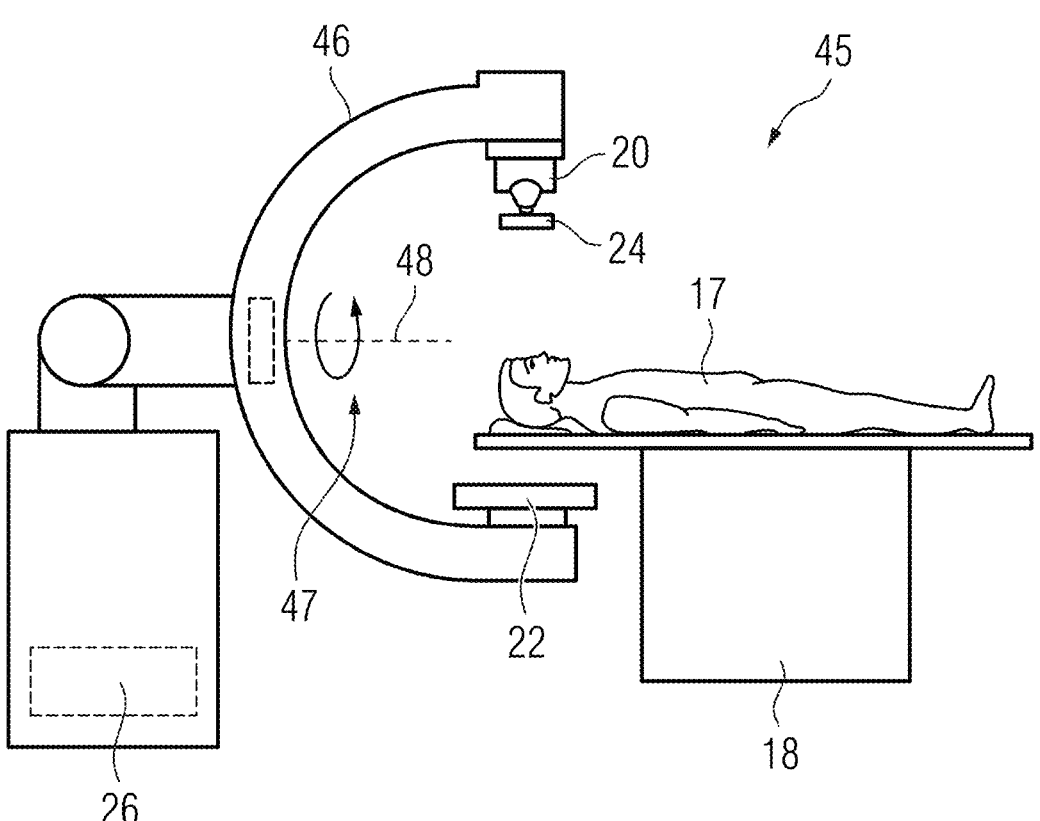
FIG. 11 depicts an X-ray facility according to a second exemplary embodiment.
FIG. 12 depicts a schematic diagram of an example of a microparticle to be used in an embolization agent.

FIG. 11 shows purely schematically a second exemplary embodiment of an X-ray facility 45, with functionally identical components being provided with the same reference numerals and for the sake of simplicity not being explained again, in particular as far as the filtering facility 24 and the control facility 26 are concerned.

The X-ray facility 45 has a C-arm 46 on which, opposing each other, the X-ray source 20 and the X-ray detector 22 are arranged. In one conceivable biplane embodiment, a second C-arm with an X-ray source 21 (with filtering facility 25) and an X-ray detector 23 may also be provided.

Because the C-arm 46, as indicated by the arrow 47, may be rotated about the longitudinal axis 48, cone beam computed tomography may be carried out controlled by the control facility 26. Two-dimensional individual applications (radiography and fluoroscopy) are also conceivable.

FIG. 12 shows, finally, one possible specific embodiment of the embolization agent 30, which in the present case is made of a large number of microparticles 39, (e.g., microbeads or micropearls). These include a hollow plastic carrier material 40 in whose interior the active ingredient 41a, for example, a chemical active ingredient for TACE and/or a radioactive active ingredient for SIRT, may be provided. The contrast material 42 may likewise be arranged, as a metal powder, in the interior cavity and/or be in the form of a coating on the outside of the plastic carrier material 40. Its quantity is selected such that the buoyancy in the blood and/or a carrier fluid, (e.g., saline solution and/or contrast agent), is compensated. The contrast material 42 imparts radiopacity to the embolization agent 30, specifically the microparticles 39, with a particularly high radiopacity being provided owing to the high atomic number. If compared, for example, with iodine, tantalum as the contrast material 42 supplies a radiopacity that is higher by the factor of 3.1, platinum supplies a radiopacity that is higher by the factor of 3.9, and bismuth supplies a radiopacity that is higher by the factor of 4.8. Therefore, a clear dose reduction is also possible, as already explained in the introduction. Using the multi-energy computed tomography imaging method, (e.g., of FIG. 1), also produces an outstanding, high-quality capacity for display in computed tomography imaging.

Although the disclosure has been illustrated and described in detail by the exemplary embodiments, it is not limited by the disclosed examples and a person skilled in the art may derive other variations herefrom without departing from the scope of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for multi-energy X-ray imaging of a field of view in order to display a contrast material, located in the field of view, the method comprising:

introducing an embolization agent into a target area of a patient, wherein the embolization agent comprises the contrast material and a chemical active ingredient and/ or radioactive active ingredient, and wherein the embolization agent accumulates on a lesion in the target area of the patient to treat the lesion;

recording two image datasets having different X-ray spectra subsequent to the introducing of the embolization agent;

combining the two image datasets;

ascertaining display information of the contrast material using the combined two image datasets; and displaying the display information of the contrast material in the field of view, wherein the contrast material has an atomic number of at least 65 and/or a k-edge of at least 60 keV, and wherein the X-ray spectra are generated by using at least one spectrally acting filter, starting from a source spectrum of an X-ray source in such a way that a value of differential spectrum has a maximum, which comprises a range, beginning at the k-edge of the contrast material, of higher absorption by the contrast material.

2. The method of claim 1, wherein the atomic number of the contrast material is at least 73.

3. The method of claim 1, wherein a breadth of the maximum is 5 to 40 keV, a portion of the maximum of the differential spectrum is at least 90%, a same source spectrum of the X-ray source is taken as a starting point for the different X-ray spectra, or a combination thereof.

4. The method of claim 3, wherein the portion of the maximum of the differential spectrum is at least 95%.

5. The method of claim 3, wherein, when using the same source spectrum, the contrast material is used as a first filter material of a first filter of at least one filter.

6. The method of claim 5, wherein a second X-ray spectrum of the different X-ray spectra is spectrally unfiltered or a filter material having a higher atomic number than the contrast material is used as a second filter material of a second filter of the at least one filter.

7. The method of claim 6, wherein the second filter material is selected such that an interval of the k-edge of the second filter material from that of the contrast material is 5 to 30 keV.

8. The method of claim 6, wherein, when the contrast material is tantalum, platinum, or gold, bismuth is used as the second filter material, or when the contrast material is holmium or ytterbium, tantalum is used as the second filter material.

9. The method of claim 1, wherein the display information is ascertained by subtraction of the image datasets, and/or wherein the display information is ascertained as a display image showing a distribution of the contrast material.

10. The method of claim 1, further comprising:

introducing an additional amount of the embolization agent into the target area of the patient as a function of the display information of the contrast material.

11. The method of claim 10, wherein the function of the display information comprises a density of the contrast material.

12. A method for imaging after an embolization procedure using an embolization agent comprising a contrast material, in a field of view of a patient, the method comprising:

introducing the embolization agent into a target area of the patient, wherein the embolization agent comprises the contrast material and a chemical active ingredient and/ or radioactive active ingredient, and wherein the embolization agent accumulates on a lesion in the target area of the patient to treat the lesion;

recording two image datasets having different X-ray spectra subsequent to the introducing of the embolization agent;

combining the two image datasets;

ascertaining display information of the contrast material using the combined two image datasets; and imaging after the embolization procedure using the embolization agent comprising the contrast material, wherein the contrast material has an atomic number of at least 65 and/or a k-edge of at least 60 keV.

13. The method of claim 12, wherein the embolization agent comprises microparticles.

14. The method of claim 12, wherein the atomic number of the contrast material is at least 73.

15. A method for imaging a contrast agent in a field of view, wherein the contrast agent has a contrast material, the method comprising:

introducing an embolization agent into a target area of a patient, wherein the embolization agent comprises the contrast material and a chemical active ingredient and/ or radioactive active ingredient, and wherein the embolization agent accumulates on a lesion in the target area of the patient to treat the lesion;

recording two image datasets having different X-ray spectra subsequent to the introducing of the embolization agent;

combining the two image datasets;

ascertaining display information of the contrast material using the combined two image datasets; and imaging the contrast agent in the field of view, wherein the contrast material has an atomic number of at least 65 and/or a k-edge of at least 60 keV.

16. The method of claim 15, wherein the atomic number of the contrast material is at least 73.

17. A system comprising:

an X-ray facility having:

a control facility; and a filtering facility comprising at least one filter, wherein the control facility is configured to:

introduce an embolization agent into a target area of a patient, wherein the embolization agent comprises a contrast material and a chemical active ingredient and/or radioactive active ingredient, and wherein the embolization agent is configured to accumulate on a lesion in the target area of the patient to treat the lesion;

record two image datasets having different X-ray spectra subsequent to the introduction of the embolization agent;

combine the two image datasets;

ascertain display information of the contrast material using the combined two image datasets; and display the display information of the contrast material in a field of view, wherein the contrast material has an atomic number of at least 65 and/or a k-edge of at least 60 keV, and wherein the X-ray spectra are generated by using the at least one filter of the filtering facility, starting from a source spectrum of an X-ray source in such a way that a value of differential spectrum has a maximum, which comprises a range, beginning at the k-edge of the contrast material, of higher absorption by the contrast material.

18. The system of claim 17, wherein the embolization agent comprises microparticles.

19. The system of claim 17, wherein the embolization agent comprises a chemical active ingredient, a radioactive active ingredient, a plastic carrier material, or a combination thereof, and wherein the chemical active ingredient and/or the radioactive active ingredient is configured for transarterial chemoembolization and/or for selective internal radiation therapy.

20. The system of claim 17, wherein a portion of the contrast material in the embolization agent is selected for minimization of a buoyancy in blood, a carrier fluid, or a combination thereof.

21. The system of claim 20, wherein the carrier fluid comprises a saline solution, a contrast agent, or a combination thereof.

* * * * *